(12) United States Patent
Farshad et al.

(10) Patent No.: US 11,730,389 B2
(45) Date of Patent: Aug. 22, 2023

(54) METHOD AND SYSTEM FOR SUPPORTING MEDICAL INTERVENTIONS

(71) Applicant: INCREMED AG, Zurich (CH)

(72) Inventors: Mazda Farshad, Zumikon (CH); Till Bay, Zurich (CH); Simon Roner, Zurich (CH); Florentin Liebmann, Zurich (CH); Florian Wanivenhaus, Zurich (CH)

(73) Assignee: INCREMED AG, Zurich (CH)

( * ) Notice: Subject to any disclaimer, the term of this patent is extended or adjusted under 35 U.S.C. 154(b) by 1163 days.

(21) Appl. No.: 16/259,768

(22) Filed: Jan. 28, 2019

(65) Prior Publication Data
US 2020/0237256 A1 Jul. 30, 2020

(51) Int. Cl.
| | |
|---|---|
| *A61B 5/00* | (2006.01) |
| *A61B 5/06* | (2006.01) |
| *G06T 7/60* | (2017.01) |
| *G02B 27/01* | (2006.01) |
| *A61B 5/107* | (2006.01) |
| *A61B 90/00* | (2016.01) |
| *G06T 7/73* | (2017.01) |
| *G06F 3/01* | (2006.01) |
| *G06F 3/16* | (2006.01) |

(52) U.S. Cl.
CPC .............. *A61B 5/064* (2013.01); *A61B 5/107* (2013.01); *A61B 90/37* (2016.02); *A61B 90/39* (2016.02); *G02B 27/0172* (2013.01); *G06T 7/60* (2013.01); *G06T 7/73* (2017.01); *A61B 2090/372* (2016.02); *A61B 2090/3916* (2016.02); *A61B 2090/3975* (2016.02); *G02B 2027/0141* (2013.01); *G06F 3/013* (2013.01); *G06F 3/017* (2013.01); *G06F 3/167* (2013.01); *G06T 2207/10081* (2013.01); *G06T 2207/10088* (2013.01); *G06T 2207/30012* (2013.01); *G06T 2207/30052* (2013.01); *G06T 2207/30204* (2013.01)

(58) Field of Classification Search
CPC combination set(s) only.
See application file for complete search history.

(56) References Cited

U.S. PATENT DOCUMENTS

2017/0258526 A1* 9/2017 Lang .................. A61F 2/389
2018/0071032 A1* 3/2018 de Almeida Barreto ....................
................................................................ G06T 19/006
2018/0125584 A1 5/2018 Lang

* cited by examiner

*Primary Examiner* — Joel F Brutus
(74) *Attorney, Agent, or Firm* — Katten Muchin Rosenman LLP

(57) ABSTRACT

A method for supporting medical interventions using an augmented reality system is disclosed, which comprises
determining, using a position marker and an electronic tracking system, positions of a set of points;
calculating a geometric shape using the determined positions of the set of points; and
displaying, on an optical head mounted display the calculated geometric shape in the field of view of a bearer of the display.
Furthermore, a system and a position marker adapted to be used for this method are disclosed.

16 Claims, 17 Drawing Sheets

  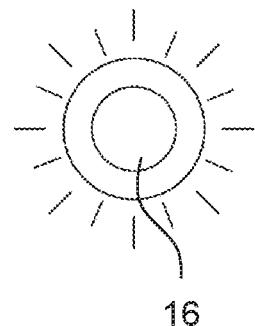
16　　　　　　　16　　　　　　　16
FIG. 7a　　　FIG. 7b　　　FIG. 7c
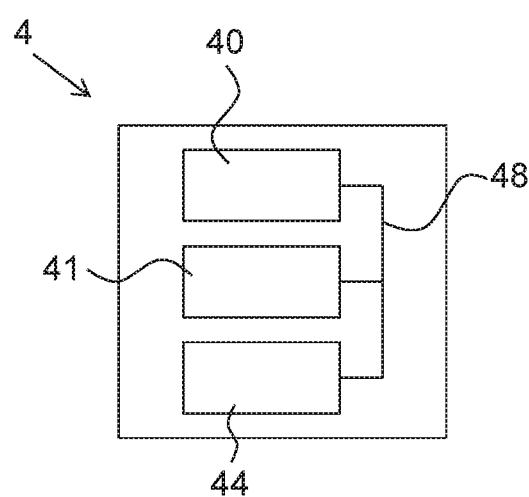
FIG. 8

METHOD AND SYSTEM FOR SUPPORTING MEDICAL INTERVENTIONS

TECHNICAL FIELD

The present invention relates to a method, a system, and a position marker for supporting medical interventions, e.g., surgical and/or diagnostic interventions. Possible applications are for example supporting sawing in the context of an osteotomy and supporting in-situ forming of a stabilizer device for stabilizing bones of a vertebrate.

There are a number of cases in which bones need to be stabilized, e.g., kept rigid, fixated, and/or aligned to other bones. In these cases often stabilizer devices, such as rods or plates, are attached to the body in order to stabilize the respective bones. For example, spinal instrumentation is used to keep the spine rigid after spinal fusion surgery. Stabilizer devices in form of rods are attached to the spine to function as an internal brace for the spine in order to hold the spine in a desired alignment. Typically, attachment implants in the form of pedicle screws are placed into two or more vertebrae and the stabilizer device is attached to the pedicle screws and thus to the vertebrae, thereby keeping the respective vertebrae in alignment.

BACKGROUND

In many cases, it is necessary to in-situ adjust the shape of the stabilizer device, e.g., in accordance to the physiology, the desired therapeutic effect and/or the exact location of the attachment implants. For example, in the case of spinal instrumentation, the rod is typically bent into the desired shape during surgery while the patient's body is still open. According to the current state of the art, the surgeon first forms a contoured phantom device from a manually formable material, and then forms the stabilizer device according to the contoured phantom device. This process is a complicated and time consuming task, and the longer this process needs, the longer the surgery takes, which not only increases the expense of the treatment, but can also result in more blood loss and lead to increased risks for the patient's health. Furthermore, inaccuracy of the formed stabilizer device can lead to various complications. Therefore, there is a need for a method and system for supporting the formation of stabilizer devices, and—more generally—for supporting medical interventions.

In recent years, optical head mounted displays ("OHMD") have become available, which a bearer can wear on his head and which comprise a display that is arranged in the field of view of the bearer. Such an OHMD is adapted so that the bearer can see at least a part of his real environment as well as computer-generated images shown in the field of view of the bearer, thereby creating an augmented reality, part of which is real and part of which is computer-generated. The computer-generated images can be displayed to simulate two- and three-dimensional objects that are shown as holograms overlaid onto the real world.

An augmented reality system ("ARS") is a system for creating an augmented reality. The ARS comprises an OHMD, to whose bearer the augmented reality is shown. Of course, an ARS can comprise two or more OHMDs, e.g., to create an augmented reality to each bearer. An ARS further comprises a tracking system ("TS"), i.e., a sensor system that allows to measure data concerning a position and/or an orientation, e.g., of the OHMD within the real world. In addition, the ARS comprises a processing unit, which e.g., can allow for processing data to be displayed on the OHMD and/or data that is measured by the TS.

SUMMARY

The present invention provides a method according to claim 1, a system according to claim 13, and a position marker according to claim 19. Further embodiments of the invention are laid down in the dependent claims and the specification.

A method for supporting medical interventions, e.g., surgical and/or diagnostic interventions, using an augmented reality system ("ARS") is proposed, which comprises:
- determining, using a position marker and an electronic tracking system ("TS") of the ARS, positions of a set of points;
- calculating a geometric shape using the determined positions of the set of points; and
- displaying, on an optical head mounted display ("OHMD") of the ARS, the calculated geometric shape in the field of view of a bearer of the OHMD.

According to some variants, the step of determining the positions of the set of points comprises:
- positioning the position marker to a point;
- measuring data concerning a position of the position marker using the TS; and
- determining a position of the point using the measured data concerning the position of the position marker.

According to some variants, the steps of positioning the position marker at a point and measuring data concerning a position of the position marker using the TS are iterated for each point of the set of points.

According to some variants, the step of measuring data concerning a position of the position marker using the TS comprises measuring, using the TS, data concerning a position and orientation of a position and orientation marker ("POM") that is fixedly attached to the position marker. Preferably the position marker comprises a pointer fixedly attached to the POM, and the step of determining, in particular a step of positioning, comprises positioning the pointer to a point whose position is to be determined.

According to some variants, the set of points comprises three points and the calculated geometric shape is a plane or a part of a plane. Preferably, such variants are used defined for defining a sawing plane for an osteotomy.

According to some variants, the calculated geometric shape is a template of a shape of a stabilizer device for stabilizing bones of a vertebrate. Preferably, such variants are used for supporting, e.g., in-situ, forming of a stabilizer device.

According to some variants, at least one point, preferably all or at least most points, of the set of points is an attachment point of an attachment implant.

According to some variants, the calculated template is displayed in a size that corresponds to a size of the stabilizer device at a distance between 1 cm and 100 cm from the OHMD. Preferably, the calculated template is displayed in a size that corresponds to a size of the stabilizer device at arm's length for the bearer of the OHMD.

According to some variants, the ARS, if the ARS automatically recognizes a stabilizer device in the field of view of the bearer of the OHMD, displays, on the OHMD, the calculated template in a position and orientation that corresponds to a position and orientation of the recognized stabilizer device relative to the OHMD.

According to some variants, the method further comprises forming the stabilizer device according to the calculated template displayed on the OHMD.

According to some variants, the template is calculated using a Spline-curve, a Spline-surface, a composite Bezier-curve, and/or a composite Bezier-surface.

According to some variants, calculating the template comprises using a pre-defined starting template. Preferably, the pre-defined starting template is defined using medical imaging comprising an X-ray/computed tomography ("CT") imaging and/or magnetic resonance imaging.

Furthermore, a system for supporting medical interventions, e.g., surgical and/or diagnostic interventions, using an augmented reality system ("ARS") is proposed, which comprises:
 a position marker; and
 an augmented reality system ("ARS"), comprising
  an electronic tracking system ("TS") that is adapted to measure data concerning a position of the position marker,
  a processing unit that is configured
   to determine a position of the position marker using data measured by the TS, and
  an optical head mounted display ("OHMD") that is designed to display images in the field of view of its bearer.

According to some embodiments, the processing unit is configured to calculate a geometric shape using a set of points; and/or the OHMD is adapted to display the geometric shape in the field of view of the bearer.

According to some embodiments, the position marker comprises a pointer and a position and orientation marker ("POM"), wherein the pointer is fixedly attached to the POM. Preferably, the TS is adapted to measure data concerning a position and orientation of the POM. The processing unit is preferably configured to determine a position and orientation of the POM using data measured by the TS. Preferably, the processing unit is configured to determine a position of the pointer using a position and orientation of the POM, and in this way determine a position of the position marker.

According to some embodiments, the system, preferably the ARS, in particular the processing unit, comprises a memory element, wherein the memory element comprises data concerning the position of the pointer relative to the position and orientation of the POM. Preferably, the processing unit is configured to determine the position of the pointer using the position and orientation of the POM and the data concerning the position of the pointer relative to the position and orientation of the POM.

According to some embodiments, the system, preferably the ARS, comprises one or more controllers, wherein the one or more controllers preferably comprise a voice controller, a gesture controller, a gaze controller and/or a physical controller.

According to some embodiments, the geometric shape is a template of a shape of a stabilizer device using a set of points. Preferably, the system is designed for supporting forming, in particular in-situ forming, a stabilizer device for stabilizing bones of a vertebrate.

According to some embodiments, the ARS is adapted to recognize a stabilizer device, e.g., a blank of a stabilizer device or an at least partially formed stabilizer device, in the field of view of the bearer of the OHMD and to display on the OHMD a calculated template of a stabilizer device at a distance and at an angle that corresponds to a distance and an angle of the recognized stabilizer device.

Furthermore, a position marker for supporting medical interventions, e.g., surgical and/or diagnostic interventions, is proposed. The position marker preferably comprises a pointer and a position and orientation marker ("POM") is proposed. Preferably, the position marker is designed for supporting forming, in particular in-situ forming, a stabilizer device for stabilizing bones of a vertebrate.

According to some embodiments, the pointer is fixedly attached to the POM. Preferably, the pointer is connected to the POM by a stick. The pointer is preferably arranged at one of the ends of the stick. Preferably, the pointer and the POM are arranged at a distance of at least 5 cm from each other. The POM preferably comprises an image pattern.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings,
FIGS. 7a-7c shows a gaze button;
FIG. 8 shows a processing unit.

DESCRIPTION OF PREFERRED EMBODIMENTS

A system for supporting medical interventions, e.g., surgical and/or diagnostic interventions, is proposed, which comprises an augmented reality system ("ARS") 2 and a position marker 5. The system is preferably configured to perform one or more of the methods disclosed herein. In particular, the system is configured for supporting forming, in particular for supporting in-situ forming, a stabilizer device for stabilizing bones of a vertebrate.

Figure 1:
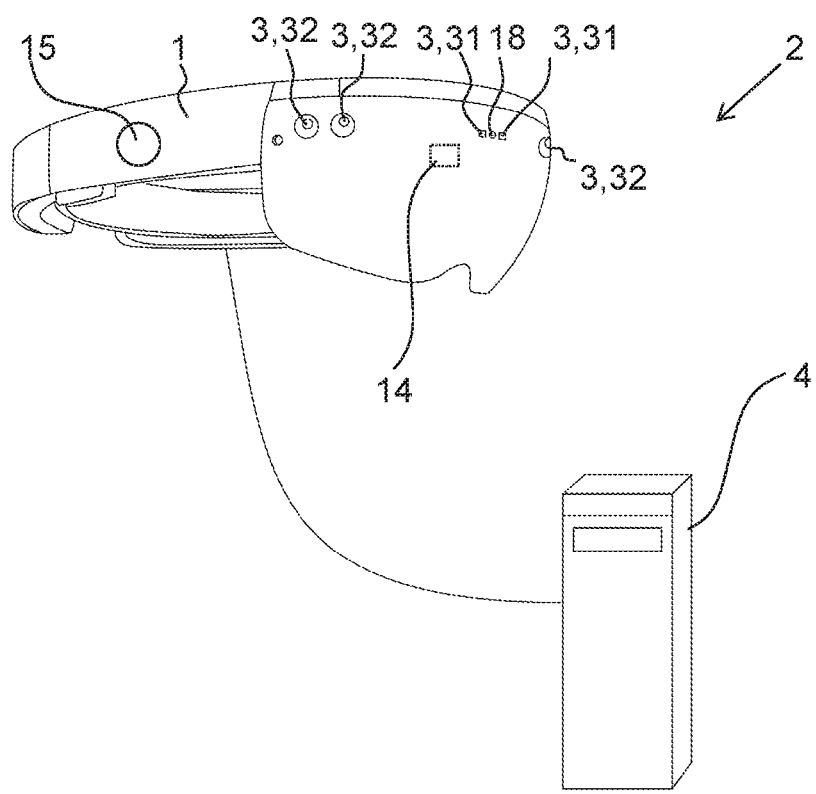
FIG. 1 shows an ARS.

FIG. 1 shows an example of an ARS 2, which comprises an optical head mounted displays ("OHMD") 1, an electronic tracking system ("TS") 3 and a processing unit 4.

The TS 3 is adapted to measure data concerning a position of the position marker 5, preferably data that allow determining the position of the position marker. Preferably, the TS 3 is adapted to measure data concerning a position and/or an orientation of a position and orientation marker ("POM") 51 of a position marker 5.

In the embodiment shown in FIG. 1, the TS 3 comprises an emitter 31 and a sensor 32 arranged at the OHMD 1. However, the TS 3 can also comprise, in particular consist of, parts that are not arranged at the OHMD 1.

The TS 3 is a sensor system and comprises one ore multiple sensor means. According to some embodiments, sensor means of the TS 3 comprise

- optical means, i.e., using electromagnetic radiation in the visible-light spectrum (between 380 nanometres and 780 nanometres);
- infrared means, i.e., using electromagnetic radiation in the infrared spectrum (between 780 nanometres and 1 millimetre);
- magnetic means, i.e., using magnetic fields;
- radio means, i.e., using electromagnetic radiation in the radio spectrum (between 300 gigahertz and 30 hertz); and/or
- image resp. shape recognition means, i.e., using image recognition resp. shape recognition.

Preferably, the measuring means are adapted to the kind of marker of the position marker 5, for example the kind of marker of a POM 51 of the position marker 5.

The processing unit 4 is configured to determine a position of the position marker 5 using data measured by the TS 3. The processing unit 4 is preferably configured to calculate, a geometric shape using a set of points, for example a set of points whose position has been determined by the processing unit 4 using data concerning a position of the position marker 5 measured by the TS 3. In some examples, the geometric shape is a template of a shape of a stabilizer device; in other examples, the geometric shape is a sawing plane for an osteotomy.

FIG. 8 shows an example of a processing unit 4 comprising a processor (CPU) 40 and a volatile (e.g., RAM) memory 41 and/or a non-volatile (e.g., a hard disk) memory 44, wherein the processor 40 communicates with the memory modules 41, 44 using one or more data buses 48.

According to some embodiments, the processing unit 4 is configured to determine a position and orientation of a POM 51 using data measured by the TS 3. Preferably, the processing unit 4 is further configured to determine a position of a pointer 53 using a position and orientation of the POM 51 to which the pointer 53 is fixedly attached, for instance by further using data concerning the position of the pointer 53 relative to the position and orientation of the POM 51.

The OHMD 1 is designed to display images in the field of view of its bearer, preferably a geometric shape that has been calculated by the processing unit 4. According to some embodiments, the system comprises two or more position OHMDs, which can allow two operators to see the calculated template, e.g., a first surgeon forming a stabilizer device and a second surgeon controlling the form of the stabilizer device.

The position marker 5 is designed to support the ARS 2, in particular the TS 3, to measure data concerning the position of a point.

The position marker 5 can be positioned to a point and the ARS 2, preferably the TS 3, can measure data concerning a position of the position marker 5, from which the ARS 2, preferably the processing unit 4, can determine a position of the position marker 5 and thus of the point. The ARS 2 can record the position of the point, e.g., in the form of coordinates relative to the OHMD 1, a world reference system or another reference system. Thereby the point is virtually marked in the ARS 2 and preferably the point is at least temporarily displayed on the OHMD 1 if the position of the point is in the field of view of the bearer. The process can be iterated to virtually mark a set of points, which the ARS 2, preferably the processing unit 4, can use to calculate a geometric shape, which can be displayed on the OHMD 1 in the field of view of the user.

According to some embodiments, the position marker 5 comprises

- an optical marker, i.e., whose position is measureable using electromagnetic radiation in the visible-light spectrum;
- an infrared marker, i.e., whose position is measureable using electromagnetic radiation in the infrared spectrum;
- a magnetic marker, i.e., whose position is measureable using magnetic fields;
- a radio marker, i.e., whose position is measureable using electromagnetic radiation in the radio spectrum, and/or
- image resp. shape recognition means, i.e., whose position is measurable using image recognition resp. shape recognition.

Preferably, the marker means are adapted to the kind of measuring means of the TS 3.

Figure 2:
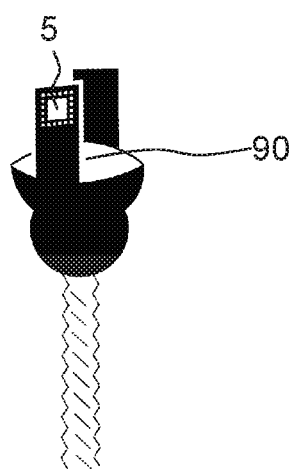
FIG. 2 shows a position marker in form of a Bluetooth-chip.
Figures 3A, 3B, 3C:
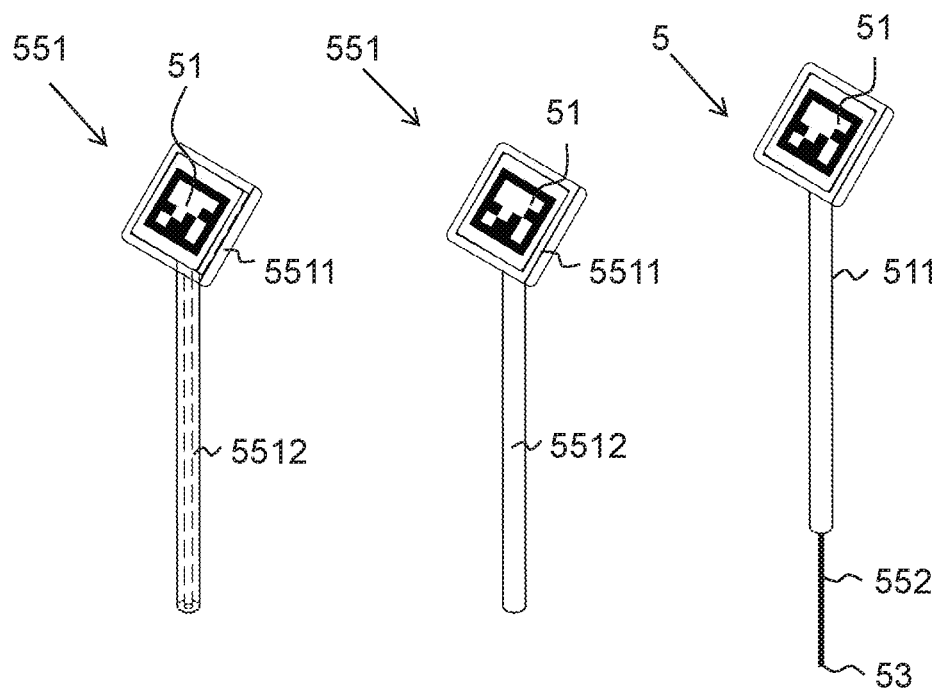
FIGS. 3a-3c shows a first position marker comprising a POM.
Figures 4A, 4B, 4C:
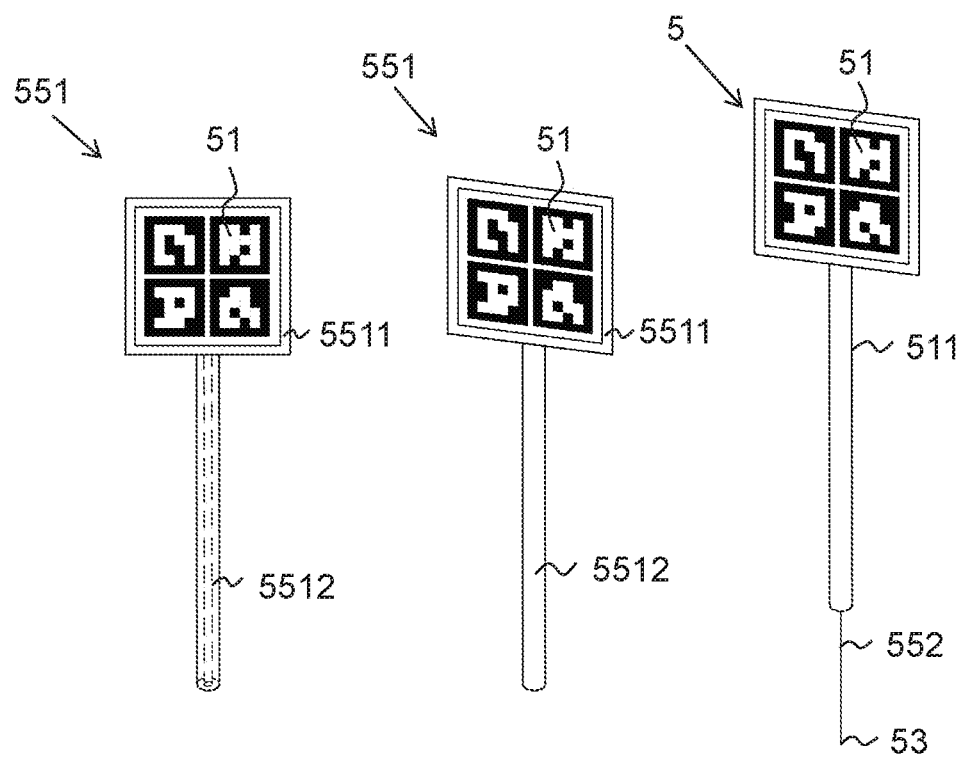
FIGS. 4a-4c shows a second position marker comprising a POM.
Figures 5A, 5B, 5C:
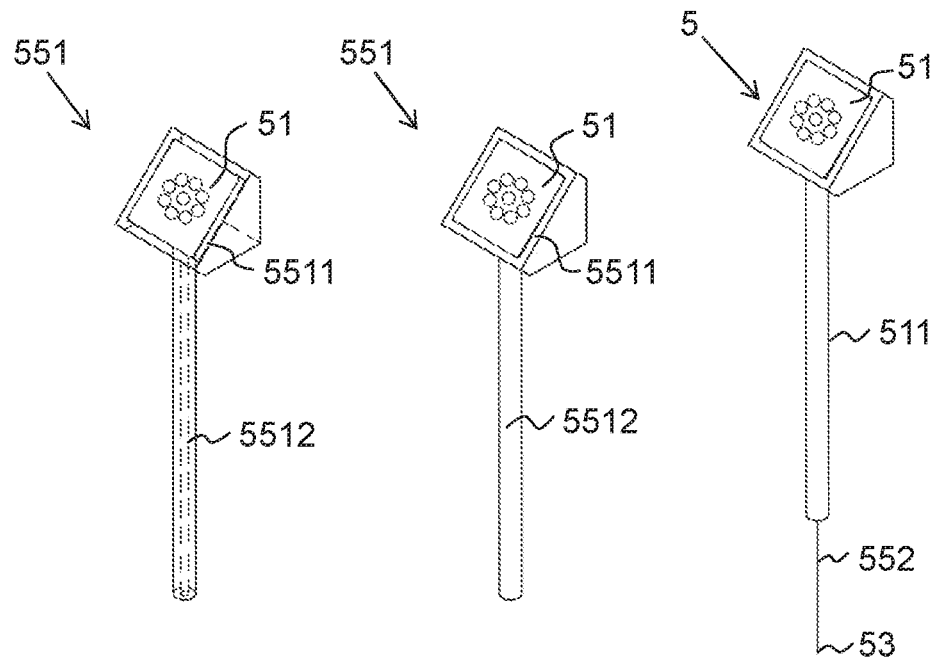
FIGS. 5a-5c shows a third position marker comprising a POM.

FIG. 2 show an example of a position marker 5 comprising a radio marker in the form of a miniature Bluetooth low energy chip that is arranged at an attachment point 90 of an attachment implant 9 in form of a pedicle screw. The TS 3 can be adapted to locate said chip 5, e.g., using another Bluetooth chip, and thus determine the position of the attachment point 90 of an implant.

According to some embodiments, the system comprises two or more position markers, which can e.g., allow for simultaneously measuring data concerning a position of the two or more position markers.

According to some embodiments, the position marker 5 comprises a position and orientation marker ("POM") 51, which is designed so that the TS 3 can measure data concerning its position and orientation. This data can be used to recognize, in particular to track, the position and orientation of the POM 51. The ARS 2, in particular the processing unit 4, can be adapted to determine a position of the position marker 5 from the position and orientation of the POM 51.

In some embodiments, the POM comprises

- an optical marker whose position and orientation is measureable using electromagnetic radiation in the visible-light spectrum;
- an infrared marker whose position and orientation is measureable using electromagnetic radiation in the infrared spectrum;
- a magnetic marker whose position and orientation is measureable using magnetic fields;
- a radio marker whose position and orientation is measureable using electromagnetic radiation in the radio spectrum, and/or image resp. shape recognition means whose position and orientation is measurable using image recognition resp. shape recognition.

FIG. 3a to FIG. 6c show examples of position markers 5 that comprise POMs 51. In the examples for FIG. 3a to FIG. 5c, the POMs 51 comprise image recognition means in form of an image pattern. The image pattern preferably comprises a plurality of vertices and edges such as e.g., a QR-code. An image pattern can be two dimensional or three dimensional, in the latter case it is also called a shape pattern. The image pattern preferably comprises at least some asymmetry that allows determining the orientation of the image pattern.

The ARS 2 can be configured to recognize an image pattern and to determine the position and the orientation of the image pattern, e.g., from the size and the angle in which the ARS 2 detects the image pattern. The image pattern can be adapted to be recognizable using visible and/or infrared radiation. For example, the TS 3 of the ARS 2 can comprise a sensor 32 in form of a camera for visible radiation to collect images on which the image pattern can be recognized using software means.

Figures 6A, 6B, 6C:
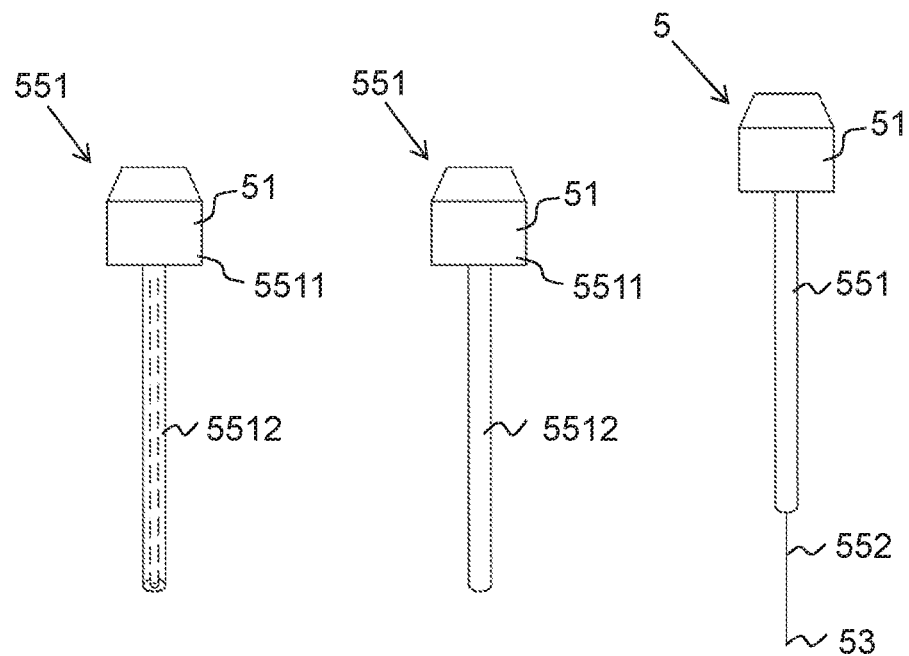
FIGS. 6a-6c shows a fourth position marker comprising a POM using magnetic means.

FIGS. 6a-6c shows an example wherein the POM 51 is a magnetic marker that comprises a coil, preferably three orthogonal coils (not visible).

According to some embodiments, the position marker 5 comprises a pointer 53. The pointer 53 is preferably a section of small diameter (e.g., less than 1 cm, preferably less than 0.3 cm) that is positioned to a point whose position is to be measured. For example, the pointer 53 can be the tip of a stick and/or a visible marking in form of an arrow.

According to some variants, the position marker 5 comprises a pointer 53 that is fixedly attached to a POM 51. Fixedly attached here means that the position of the pointer 53 relative to the POM 51 is fixed. In this case, the ARS 2 can be configured to track the position and orientation of the POM 51 and, because they are fixedly attached to one another, thus the position of the pointer 53. Thereby, the ARS 2 can determine the position of a point at which the pointer 53 is positioned by tracking the POM 51.

According to some embodiments, the system comprises a memory element, e.g., a non-volatile memory 44 and/or a volatile memory 41. Preferably, the memory element comprises data (e.g., calibration data) concerning the position of the pointer 53 relative to the position and orientation of the POM 51. The ARS 2, in particular the processing unit 4, can be configured retrieve this information from the memory element and to use it for determining the position of the pointer 53 using the position and orientation of the POM 51.

According to some embodiments, the POM 51 is arranged at a distance at least 5 cm, preferably at least 7 cm, from the pointer 53. In surgical applications, points to be measured are parts often located inside the body of a vertebrate, for example the attachment point of an affixed implant. During surgery, these points may be accessible, but due to blood, skin etc. the quality of tracking the POM 51 may be hindered in case the pointer 53 is too close to the POM 51. Thus, designing the pointer 53 to be at a certain distance from the POM 51 can allow positioning the pointer 53 to a point inside the body, while the POM 51 is located outside the body, which can support recognition of the POM 51, for instance the optical recognition of an image pattern thereof.

According to some embodiments, the pointer 53 is connected to the POM 51 by a stick 52, whose diameter is preferably less than 1 cm, for example less than 0.3 cm. Preferably, the pointer 53 is arranged at one of the ends of the stick 52.

In the examples shown in FIGS. 3c, 4c, 5c, and 6c, the pointer 53 is arranged at one end of the stick 52 and the POM 51 is arranged at the other end of the stick 52. In each of these examples, the pointer 53 is the tip of the stick 53 by which it is fixedly attached to the POM 51, which in the examples of FIGS. 3a to 5c comprises an image pattern and in the example of FIGS. 6a-6c comprises a magnetic position and orientation marker. Of course, other kinds of POMs 51 are feasible as well. The ARS 2 can be adapted to recognize the POM 51, to determine a position and orientation of the POM 51, and to determine therefrom, possibly using calibration data, the position of the pointer 53. Thereby, the ARS 2 can determine the positon of a point to which the pointer 53 is positioned. In other words, the ARS 2 in this case does not directly measure the point resp. the position of the pointer 53, but rather the positon and orientation of the POM 51. The information of the position of the pointer 53 relative to the POM 51 can e.g., be received from the image pattern of the POM 51 and/or retrieved form a memory element 41, 44.

As shown in FIGS. 3a to 6c, the position marker 5 can comprise two parts, a first part 551 comprising the POM 51 and a second part 552 comprising the pointer. As shown in FIGS. 3b, 4b, 5b, and 6b, the first part 551 comprises a head 5511 (comprising the POM 51) and a shaft 5512. The second part 552 is designed as an elongated cylinder. Preferably the first part 551 is made of plastic and the second part 552 is made of metal. As shown in FIGS. 3a, 4a, 5a, and 6a, the shaft 5512 is hollow so as to accommodate at least a part of the second part 552. Preferably, there is a well-defined stop inside the shaft 5512 to which a first end of the second part 552 can abut, so that the position of the pointer 53 at the other end of the second part 553 relatively to the first part 551 and thus to the POM 51 can be standardized. The stick 53 in the examples shown in FIGS. 3a to 6c comprise parts of the first part 551 as well as parts of the second part 552.

According to some embodiments, the ARS 2 comprises one or more controllers 15, 16, which the user, e.g., a bearer of the OHMD 1, can use to give commands to the ARS 2. For instance, the user can use the controller to virtually mark points, adjust perspectives of a displayed image, or interact with a menu. A controller can comprise hardware means and/or software means.

According to some embodiments, the ARS 2 comprises a voice controller. The voice controller allows a user to give commands using sound, in particular speech. The ARS 2, in particular the OHMD 1, preferably comprises one or more microphones for recording sound. Preferably, the ARS 2 is configured to extract information from recoded sound.

According to some embodiments, the ARS 2 comprises a gesture controller. The gesture controller allows a user to give commands using gestures. The ARS 2, in particular the TS 3, preferably comprises one or more cameras 18 for detecting gestures. The camera 18 can as well serve as a sensor 32 for marking points. Preferably, the ARS 2 is configured to extract information from gestures.

According to some embodiments, the ARS 2 comprises a gaze controller. An example of a possible design of a gaze controller in form of a gaze button 16 is shown in FIGS. 7a-7c. Here, the gaze button 16 is implemented as a circular progress bar, which indicates the duration of the bearer's gaze. It can be configured in such a way that the bearer is required to gaze at a certain position, preferably a position where the gaze button is displayed, for a prescribed amount of time, e.g., for 2 seconds, until an action is triggered. FIG. 7a shows the gaze button 16 in a default state in which the gaze button 16 is displayed in a neutral background colour.

Once the bearer of the OHMD starts gazing at the gaze button 16, it starts to fill up with a contrasting foreground colour, for example in a counter-clockwise direction as shown in FIG. 7b. If the bearer looks away from said certain position, the gaze button 16 quickly resets to its default state. However, if the gaze is held for a prescribed amount of time without interruption, the foreground colour will fill the entire button and an additional visual cue is provided to indicate that a certain action has been triggered, e.g., by a flashing light, as indicated in FIG. 7c. The OHMD 2 can comprise pupil sensors 14 that allow tracking the position of the pupils of the eyes of the bearer. The pupil sensors 14 can furthermore be used to adjust the displayed image to the bearer's physiognomy. This can e.g., entail the adjustment of the stereo-displaying in accordance with the bearer's inter-pupillary distance, and/or the scaling of the image in accordance with the distance of the bearer's pupils from mirrors of the OHMD 1. Of course, sensor means other than the pupil sensor 14 can be used for the gaze controller. For example, the ARS can be configured to determine a gazing using the orientation of the OHMD 1, i.e., the orientation of the head of the bearer.

According to some embodiments, the ARS 2 comprises a physical controller 15. A physical controller 15 in form of a physical button arranged at the OHMD 1 is shown in FIG. 1, but other types of physical controllers, such as a wheel, a joystick and/or a mouse, are possible as well.

A first controller can be used to active a second controller. For example, the user can press a physical controller 15 to activate the display of a gaze controller 16 (such as e.g., shown in FIG. 7a) and a respective gazing tracking.

According to some embodiments, the ARS 2 is configured for adjusting the position and orientation of an image displayed on the OHMD 1. Such an adjustment can be triggered by a user command initiated via a controller 15, e.g., a voice command for zooming, panning, and/or rotating the image.

Figure 24:
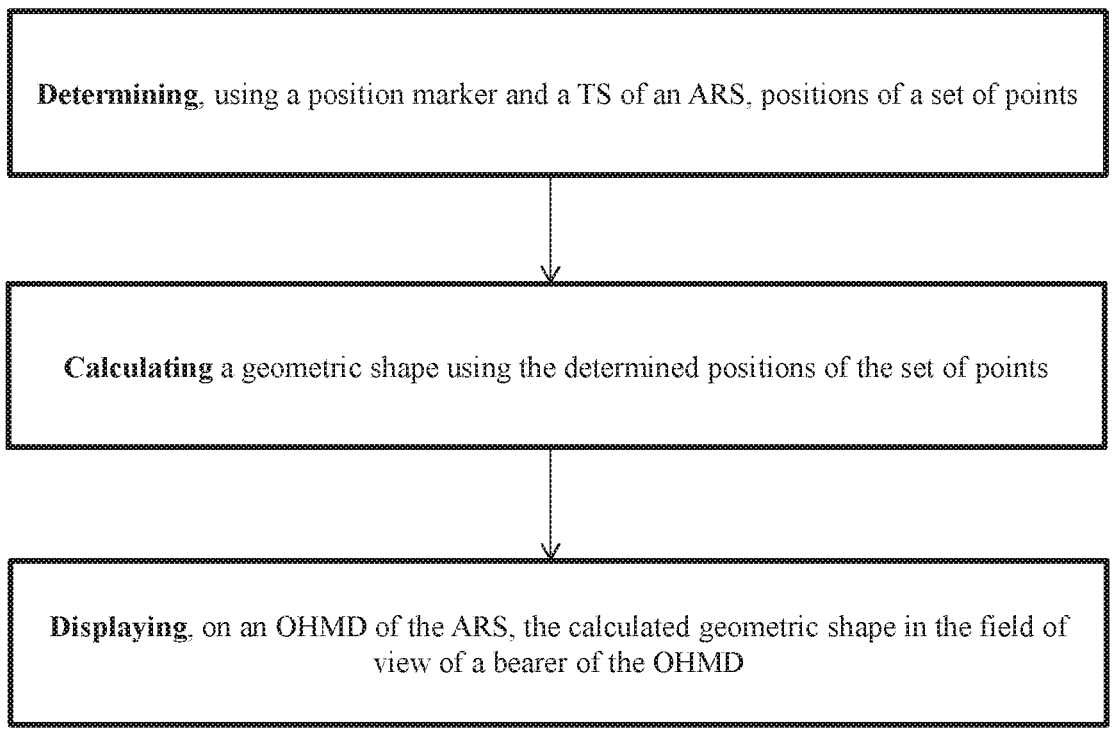
FIG. 24 shows a first flow diagram.

According to some embodiments, the ARS 2 is configured to adjust the position and orientation of a displayed image automatically. In an example, the ARS 2 is configured to automatically adjust the position and orientation of the displayed image to overlay and adjust to a recognized object in the field of view of the bearer, e.g., a moving body part of which the displayed image is an image of or a moved stabilizer device 7 of which the displayed image is a template of A method for supporting medical interventions, e.g., surgical and/or diagnostic interventions, using an augmented reality system ("ARS") 2 is proposed. As shown in FIG. 24, the method preferably comprises:
 determining, using a position marker 5 and an electronic tracking system ("TS") 3 of the ARS, positions of a set of points 8;
 calculating a geometric shape 80 using the determined positions of the set of points 8; and
 displaying, on an optical head mounted display ("OHMD") 1 of the ARS 2, the calculated geometric shape 80 in the field of view of a bearer of the OHMD 1.

Figure 25:
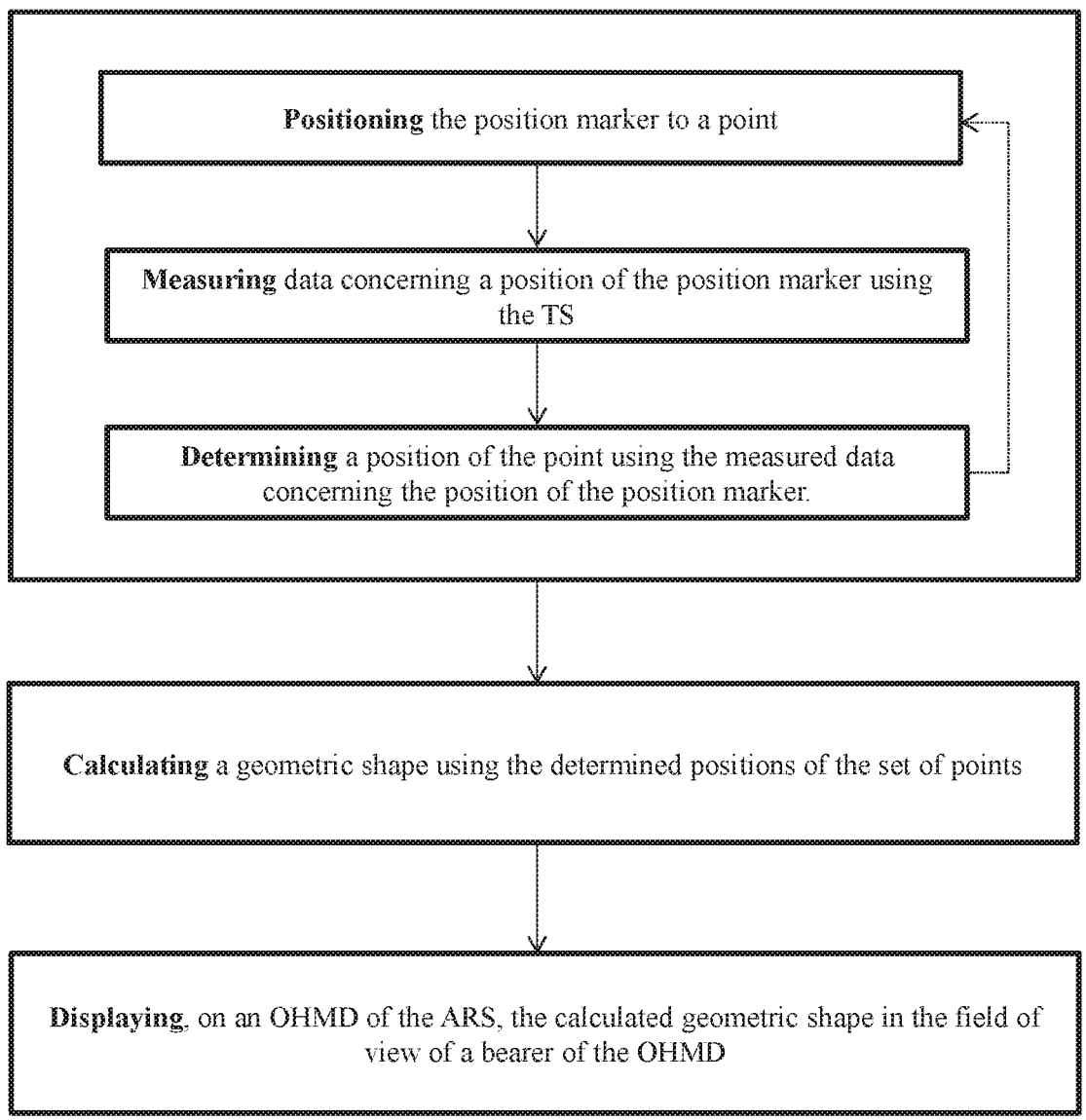
FIG. 25 shows a second flow diagram.

As shown in FIG. 25, the step of determining the positions of the set of points 8 preferably comprises:
 positioning the position marker 5, in particular a pointer thereof, to a point 8;
 measuring data concerning a position of the position marker positioned to said point using the TS 3; and
 determining a position of the point using the measured data concerning the position of the position marker.

Figure 26:
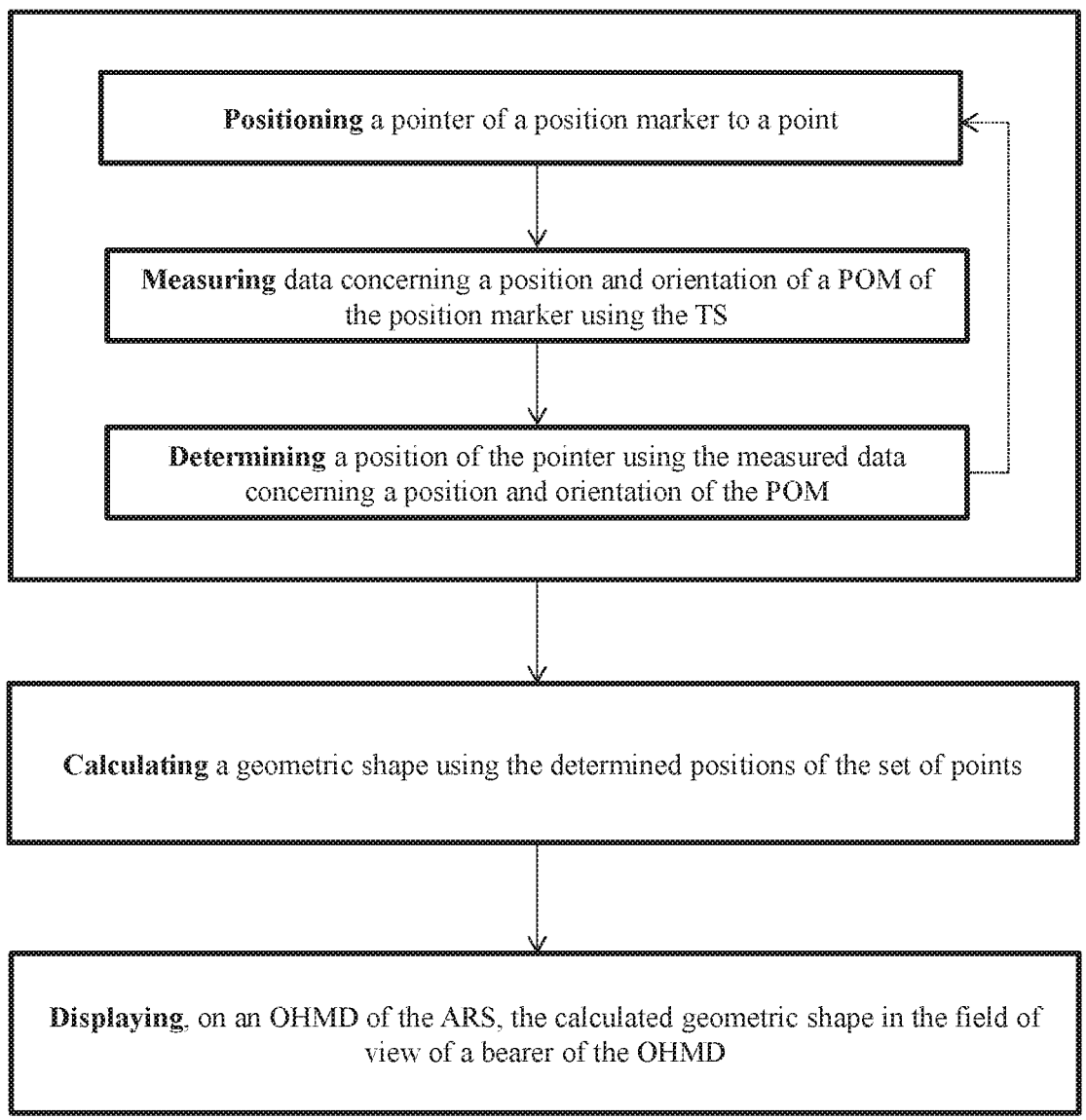
FIG. 26 shows a third flow diagram.

As shown in FIG. 26, for determining preferably comprises determining a position of a pointer 53 using measured data concerning a position and orientation of a POM 51, possibly using additional information, such as a relative positioning between the pointer 53 and the POM 51 and/or other calibration data.

Figure 9:
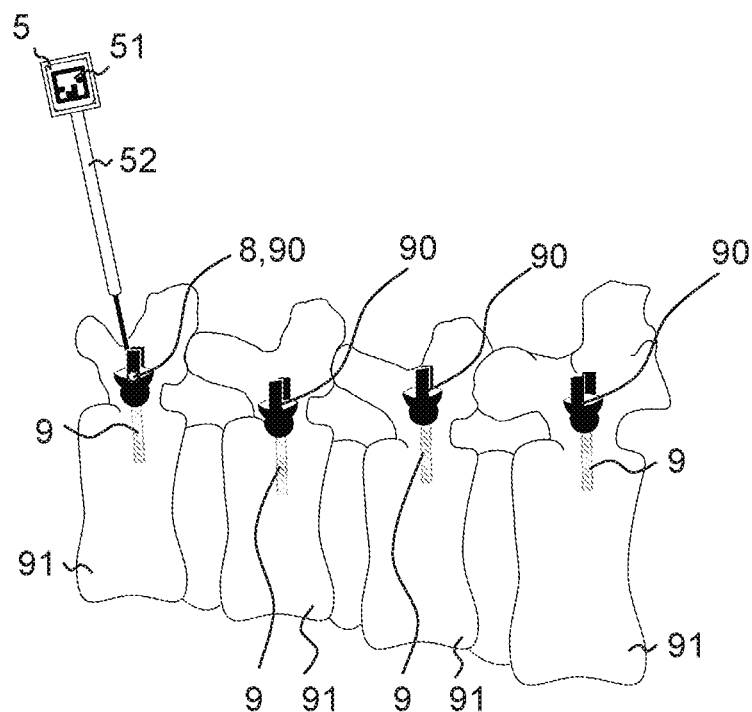
FIG. 9 shows a first state of marking a set of points.
Figure 10:
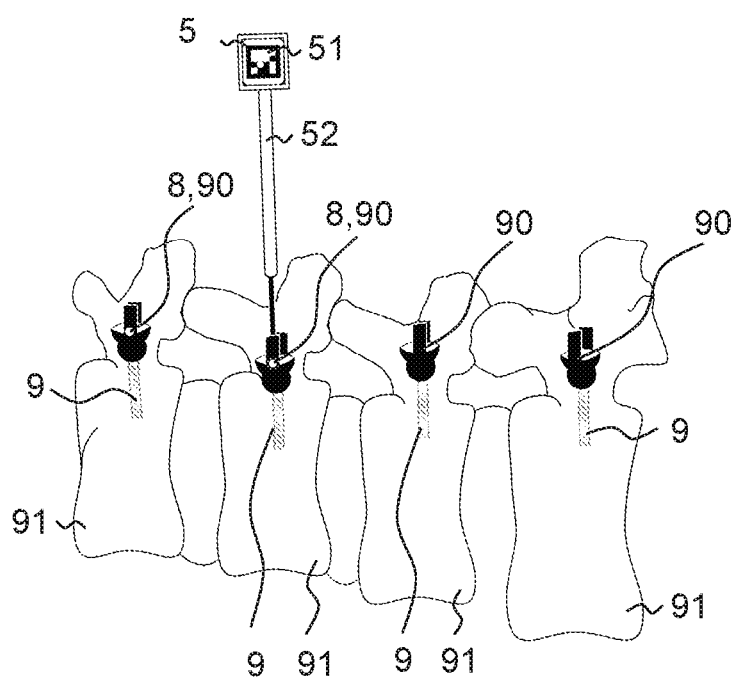
FIG. 10 shows a second state of marking a set of points.
Figure 11:
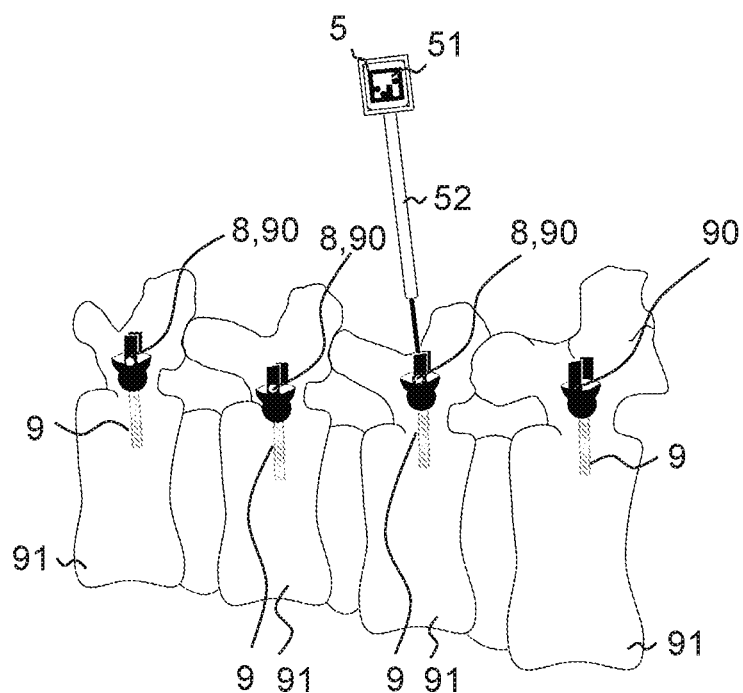
FIG. 11 shows a third state of marking a set of points.
Figure 12:
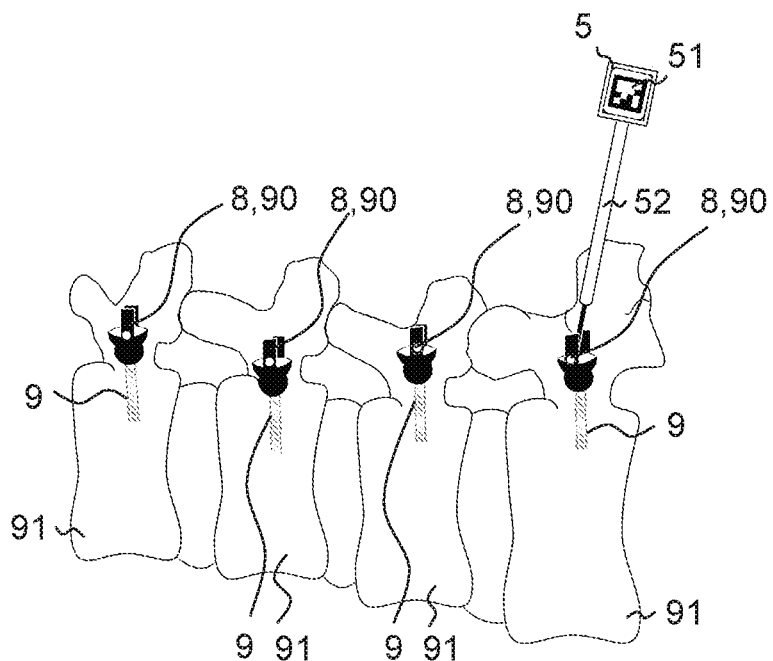
FIG. 12 shows a fourth state of marking a set of points.

In the example of FIG. 9, attachment implants 9 in form of pedicle screws are affixed to four vertebrae 91 for a spinal instrumentation, for which a stabilizer device is to be attached to the attachment points 90 of the pedicle screws 9. The position marker 5 is positioned to the attachment point 90 in that the pointer is positioned at a first attachment point. A user of the ARS 2, e.g., the bearer of the OHMD 1, initiates a measurement, e.g., by issuing a respective command using a controller 15. In this example, the ARS 2 measures data concerning the position and orientation of the POM 51, from which it calculates the position of the pointer 53 and defines this as the position of the first points 8. In other examples, this last step might involve calculation, e.g., where the first point 8 is defined to be at a certain location relative to the pointer 53. The position of the first point 8 is recorded by the ARS 2 and the so marked first point 8 can, as shown in FIG. 9, be displayed in the field of view of the bearer of the OHMD 2. As indicated in FIG. 25, this process can be iterated so as to mark a second point 8 (FIG. 10), a third point 8 (FIG. 11) and a fourth point 8 (FIG. 12). Preferably, the ARS 2 records the order in which the marked points were measured.

According to some variants, the steps of positioning the position marker 5 at a point 8 and measuring data concerning a position of the position marker 5 using the TS 3 are iterated for each point 8 of the set of points whose position is to be determined, i.e., the position marker 5 is put to one point 8 after the other and each time data concerning the position of the position marker is measured and recorded. Of course, multiple position markers 5 can be positioned to all points 8 or a subset of the set of points, and the data concerning their position can be measured simultaneously. The step of determining can be performed for one, multiple and/or all of the points 8 at a time. Preferably, the step of determining of the position of a point 8 is performed in timely proximity to the step of measuring data concerning a position marker 5 positioned to that point 8, e.g., so that the point 8 can be displayed in the OHMD 1 shortly after the measurement, which e.g., can allow a user to check if the marking is accurate.

According to some variants, the user of the ARS 2, in particular a bearer of the OHMD 1, can adjust a perspective in which the calculated geometric shape is displayed. For example, the user can adjust a distance and/or an angle of the geometric shape, e.g., in that she can zoom in and out, pan and/or rotate the geometric shape. In the context of forming a stabilizing device, this can allow the user to match the perspective in which the calculated template is displayed to the perspective in which the bearer holds the stabilizer device.

According to some variants, the calculated and displayed geometric shape 80 is a template of a shape of a stabilizer device 7 for stabilizing bones of a vertebrate. Such stabilizer device 7 can e.g., be a bent rod or a bent plate that is formed in that it is bent from a blank (such as a default shaped rod or plate, e.g., a straight rod or a flat plate) into a desired form. The stabilizer device can be designed as an implant and/or as an external device. Stabilizer devices are e.g., used for spinal instrumentation or in treating fractures such as pelvic fracture, clavicle fracture, or alike.

Figure 13:
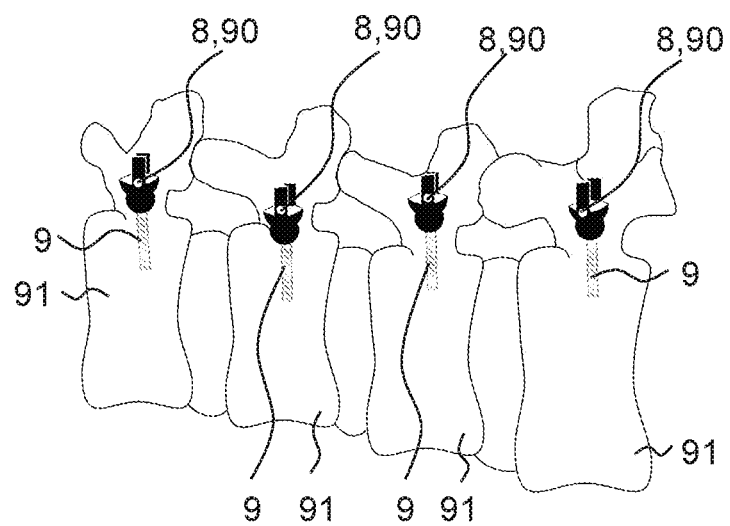
FIG. 13 shows a set of marked points in an implant setting.

As exemplified in FIG. 13, the set of points 8 preferably comprises attachment points 90, i.e., points to which the stabilizer device 7 is attached in course of a treatment. Attachment points 90 can for example be points of attachment implants 9 that are designed so that the stabilizer device 7 can be attached to these points and thereby be attached to the bones to which the attachment implants 9 are affixed. In the example of FIG. 13, the attachments points 90 can be the heads of pedicle screws which—together with suitable counterparts (not shown)—form of grommets in which a the stabilizing rod 7 can be attached.

The set of points 8 can relate to points of the anatomy as it currently is ("current status"). In an example, the set of points 8 is a set of attachment points 90 of attachment implants 9 that are affixed to bones 91 in their current positon. In case the template is calculated so that it can pass through every point of this set of points 8 and the stabilizer device 7 is formed according to this template 80 and attached to the attachment implants 9 at their respective attachment points 90, the bones 91 are stabilized according to their current status. Such method can be used for preserving a current status.

The set of points 8 can relate to points of the anatomy as it is planned to be ("target status"). In an example, a vertebra B is intended to be moved and the two neighbouring vertebrae A and C are intended to remain at their respective positions. The operator determines the attachment points 90 relating to vertebrae A and C according to where they currently are and the attachment points 90 relating to vertebra B according to where the operator plans to move vertebra B. In case the template is calculated so that it can pass through every point of this set of points 8 and the stabilizer device 7 is formed according to this template 80 and attached to the affixed attachment implants 9 at their respective attachment points 90, the bones 91 are stabilized according to their target status. Such method can be used for correcting of displaced bones 91. In some variants, the method comprises defining a target status of an anatomy, determining the position of a set of points of a current status of an anatomy and calculating a template 80 of a shape of the stabilizer device 7 so that if the stabilizer device 7 is formed according to that template 80, the stabilizer device 7 stabilizes the anatomy according to the target status.

Figure 14:
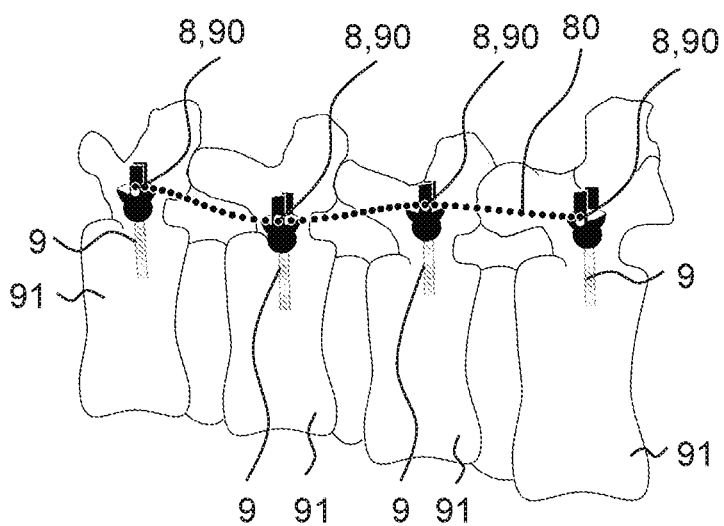
FIG. 14 shows a geometric shape in an implant setting.

FIG. 14 shows an example where the current status is the target status of the vertebrae 91. The attachment points 90 have been marked and the geometric shape 80 of a template of a shape of a stabilizer device 7 has been calculated. In this example the calculated template 80 is displayed on the OHMD 2 at the location where the formed stabilizing device 7 will be arranged.

In some embodiments, the stabilizer device is formed in that it is created, e.g., by a 3D-printing process.

Figure 27:
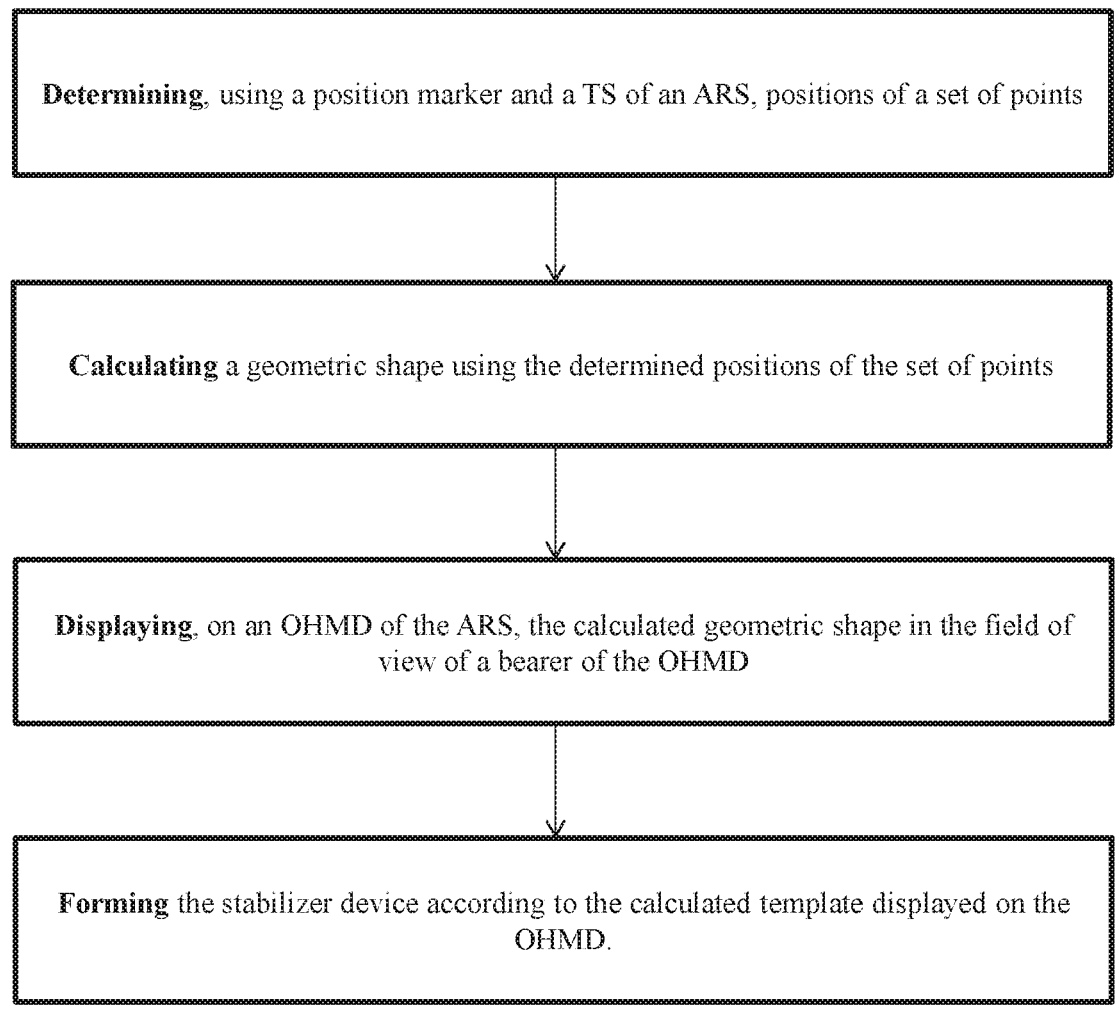
FIG. 27 shows a fourth flow diagram.

As shown in FIG. 27, the method can further comprise the formation of a stabilizer device according to the calculated template displayed on the OHMD 2.

Figure 15:
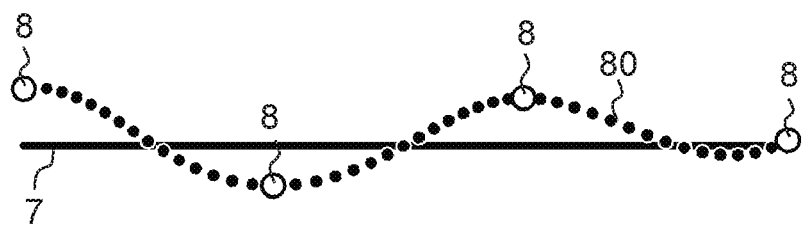
FIG. 15 shows a blank and a template.
Figure 16:
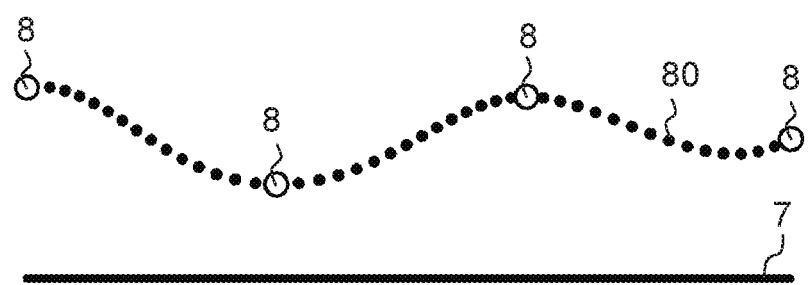
FIG. 16 shows the blank and the template at a distance.

FIG. 15 shows a geometric shape 80 in form of a template 80 of a shape of a stabilizer device 7 being displayed such that, from the view of the bearer of the OHMD, the hologram 80 of the template lays over a real-world blank 7 that is to be formed into the desired stabilizer device according to the template 80. Similarly, FIG. 16 shows the configuration of FIG. 15, but wherein the template 80 is displayed at a distance from the blank 7.

Figure 19:
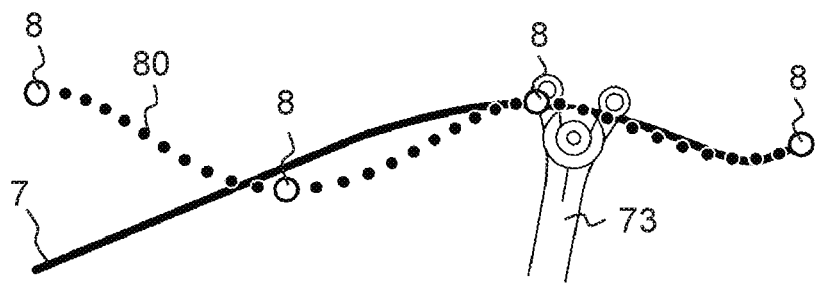
FIG. 19 shows a blank being formed and a template.
Figure 20:
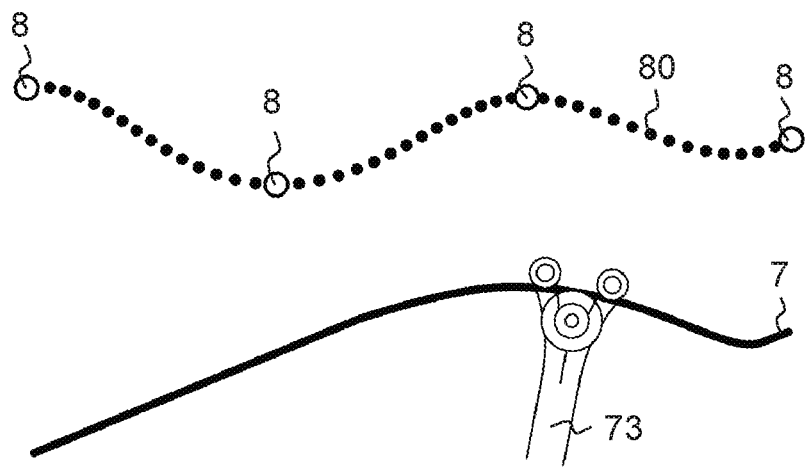
FIG. 20 shows the blank being formed and the template at a distance.
Figure 21:
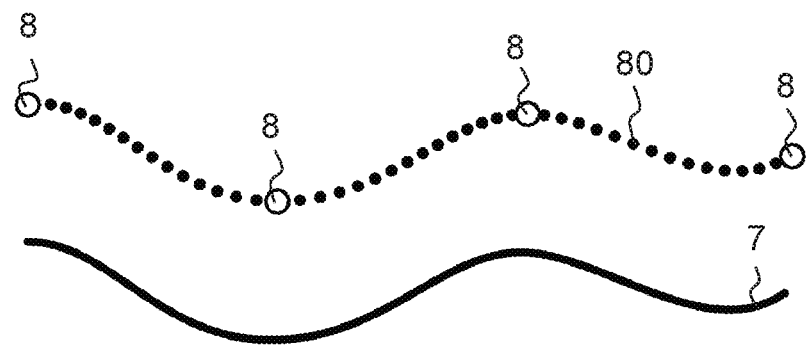
FIG. 21 shows a formed stabilizer device and a template.

As shown in FIG. 19, the blank 7 can be formed in that it is bent according to the template 80, preferably by using an adequate tool such as a French bender 73. Using the proposed method can allow forming the stabilizer device faster and/or more accurately. FIG. 20 shows the configuration of FIG. 19, but wherein the template 80 is displayed at a distance from the blank 7. Finally, FIG. 21 shows the template 80 and at a distance a stabilizer device 7 that has been bent according to the template 80.

According to some variants, the forming is performed by the bearer of the OHMD 2. Of course, the forming can also be performed by someone or something else, and the bearer of the OHMD 2 can use the displayed template 80 to control the result of the forming. The forming can e.g., comprise creating a stabilizer device (e.g., by 3D-printing) and possibly reworking the created stabilizer device.

According to some variants, the calculated template 80 is displayed on the OHMD 2 in a size that corresponds to a size of the stabilizer device 7 at a distance between 1 cm and 100 cm, preferably between 20 cm and 60 cm, of the OHMD 2. Preferably, the calculated template 80 is displayed in a size that corresponds to a size of the stabilizer device 7 at a distance arm's length of the bearer of the OHMD 2 so that a stabilizer device 7 held by a bearer of the OHMD 2 is comparable to the displayed template 80 in size.

According to some variants, the calculated template 80 is displayed in a size according to the actual size of the stabilizer device 7, i.e., 1:1 to reality. Preferably, individual data, such as e.g., the pupil distance of a bearer, is determined and the displayed image is adjusted so that the image appears to the individual bearer at the intended position and in the intended size.

Figure 17:
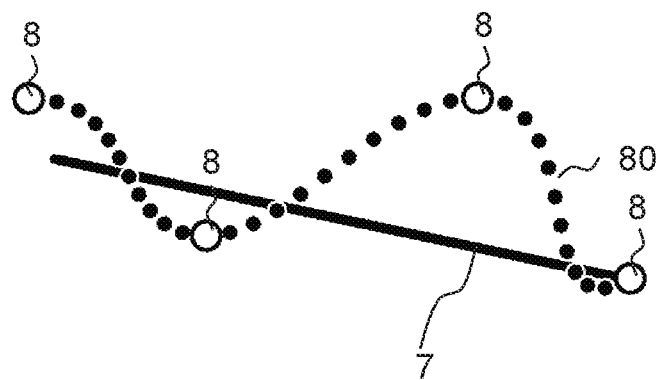
FIG. 17 shows the blank and the template from a second perspective.
Figure 18:
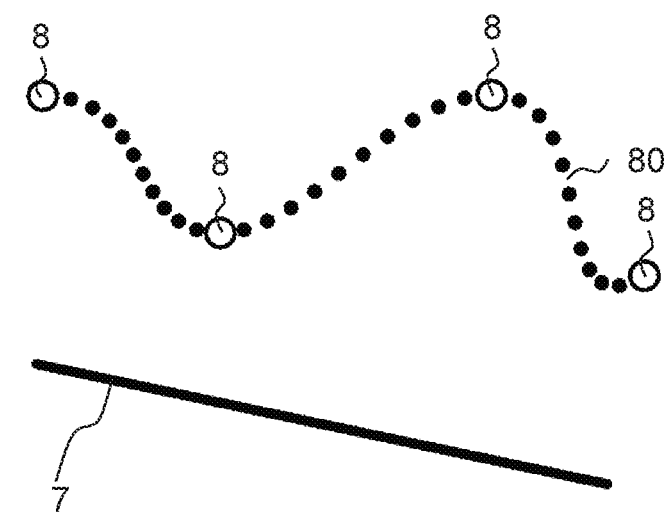
FIG. 18 shows the blank and the template at a distance from a second perspective.

According to some variants, the ARS 2 is adapted to automatically recognize a stabilizer device 7 (resp. a blank or a partly formed blank thereof) in the field of view of the bearer of the OHMD 1. Such recognition can for example be performed using the TS 3 and an image recognition algorithm, e.g., using artificial intelligence. Preferably, the ARS 2 is further adapted to automatically recognize a position and orientation of the stabilizer device 7 in its field of view. The ARS 2 is preferably adapted to display, on the OHMD 1, the template 80 from a perspective (relative to the OHMD 1) that corresponds to the recognized position and orientation of the stabilizer device 7. This can allow the bearer of the OHMD 2 to move the stabilizer device 7, e.g., during forming, while seeing the displayed template adjusted to the respective position and orientation of the stabilizer device. For example, in FIG. 17 resp. FIG. 18 the blank of a stabilizing device 7 of FIG. 15 resp. FIG. 16 has been rotated and the ARS 2 has automatically adjusted the perspective from which the template 80 is displayed to match the new position and orientation of the blank 7.

Alternatively, a user can move, rotate, pan, and/or zoom in/out of the hologram 80 to match the new perspective of the stabilizing device 7.

Figure 22:
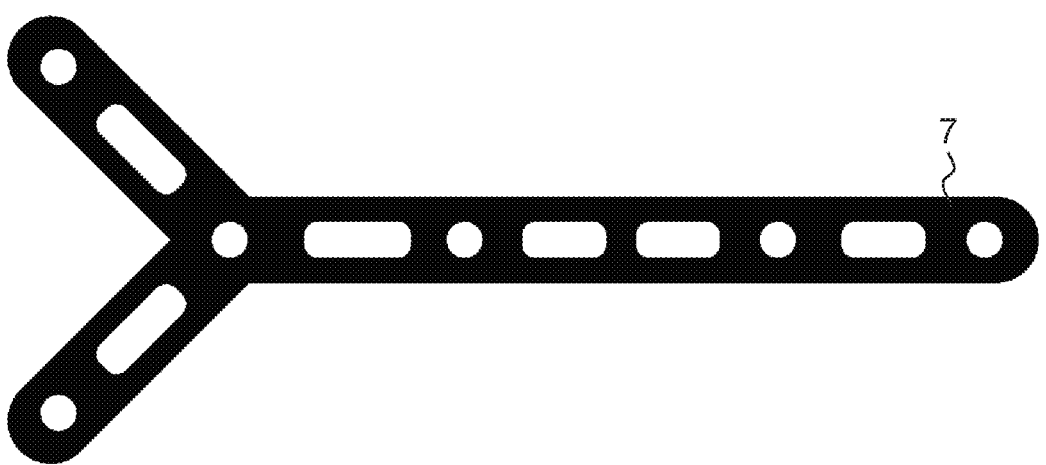
FIG. 22 shows a blank of a plate.

For some treatments, the stabilizer device 7 preferably is a plate, such as the one shown in FIG. 22. Similar to the case of a rod, a template 80 for a plate 7 can be calculated and displayed to support the formation of the plate 7. A plate 7 can e.g., used for stabilizing a bone after an osteotomy.

The calculated template 80 of the stabilizer device 7 preferably has a smooth geometric form. According to some variants, the template is calculated using a Spline-curve, a Spline-surface, a composite Bezier-curve and/or a composite Bezier-surface. The Spline is preferable a cubic Hermite Spline, e.g., computed according to Centripetal Catmull-Rom conditions. Of course, other mathematical concepts, such as minimal surfaces etc., can be used as well. Preferably, the template 80 is calculated so that it passes through every point of the set of points 8. In an example, the template is a Catmull-Rom Spline whose control points are the set of points 8.

In many cases, the stabilizer device 7 is intended for stabilizing the bones in a target status other than the current status. In these cases the target status is often pre-defined before a surgery, e.g., using medical images, which allows for creating a pre-defined template. In practice, this pre-defined template often needs to be adapted to the current status. However, these pre-defined can be used as starting template to calculate the template.

Figure 28:
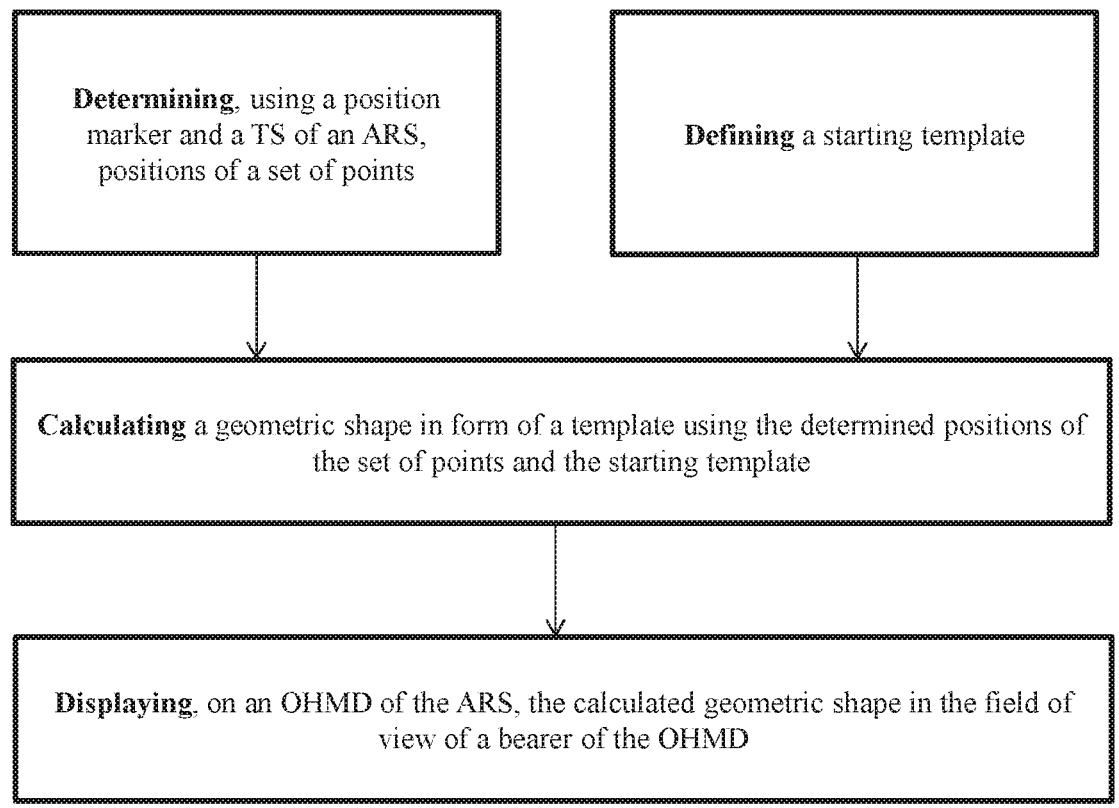
FIG. 28 shows a fifth flow diagram.

According to some variants such as e.g., shown in FIG. 28, calculating a template 80 of a shape of a stabilizer device 7 uses the determined positions of a set of points as well as a pre-defined starting template. In an example, the pre-defined starting template is made for three attachment points 90, but during the surgery the surgeon decides to use a fourth attachment point 90. The surgeon marks the fourth attachment point 90 as well as one or more of the initially planned attachment points 90 using the position marker 5. The ARS 2 calculates a new template 80 using the pre-defined starting template as well as the determined position of the marked points. In this case the calculated template 80 could e.g., be a prolongation of the pre-defined starting template.

According to some variants, the pre-defined starting template is defined using medical imaging, e.g., X-ray imaging, computed tomography ("CT") imaging, and/or magnetic resonance imaging.

According to some variants, data concerning the pre-defined starting template is imported to the ARS 2. In an example, the pre-defined starting template is defined using a separate system and the relevant data is then imported to the ARS 2, e.g., prior or during the surgery.

Figure 23:
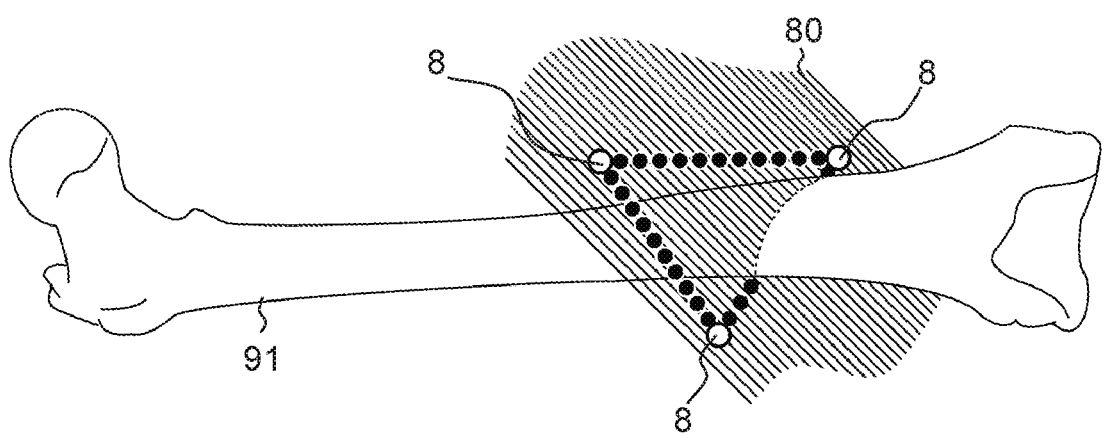
FIG. 23 shows a part of a plane.

FIG. 23 shows another application of the proposed method. In this variant, a position of three points 8 is determined and the plane 80 (resp. a part thereof) defined by the determined positions of these three points 8 is calculated. A part of this plane 80 is displayed on the OHMD 1. As shown in FIG. 23, the part of the plane 80 preferably comprises the three points 8. This variant can be used to define and display sawing planes, e.g., for an osteotomy. In this variant, the plane 80 preferably is displayed at a constant position and orientation, e.g., corresponding positon and orientation of the sawing plane.

In some variants, the augmented reality displayed to the bearer of the OHMD 2 comprises a medical image, such as a as an X-ray image, a computed tomographic ("CT") image and/or a magnetic resonance image. The medical image can be a processed version of a medical image as originally taken. For example, the displayed medical image can be processed to show the bones according to a target status.

In some variants, the medical image is displayed according to a fixed position, orientation and size relative to a world reference system and automatically adjusted as to fit the current perspective to the OHMD 2. Preferably, the position, orientation and size is fixed so that the medical image overlays a part of a body of a patient in accordance with the content of the image. In an example, the position, orientation and size of a CT image of a number of vertebrae of a patient is fixed so as to match the respective vertebrae of said patient lying on an operating table, so that the bearer of the OHMD 2 sees the CT image version of the vertebrae where the actual vertebrae are.

In an example, the fixed position, orientation and size is defined by a user of the ARS 2, e.g., using gesture control. In another example, the fixed position, orientation and size is defined by a medical imaging device that took the medical image, e.g., where the medical device is taken during an operation and the patient's body part of which the image was taken is still in the position in which the image was taken. In yet another example, the fixed position, orientation and size is defined by the ARS 2. The ARS 2 can e.g., use image recognition so as to match the medical image with the respective part of a patient, for instance by using an artificial intelligence. In some variants, position markers are used to support the ARS's 2 tracking of the position and orientation of the respective part of the patient's body. Of course, the fixed position, orientation and size can be redefined, e.g., where the respective body part is moved. Preferably, the ARS 2 tracks its own positon and orientation relative to the world reference system and uses this information to automatically adjust the image.

According to some variants, the method comprises
defining a target status of an anatomy of a patient,
overlaying of a medical image showing the target status over the respective part of the patient's anatomy,
determining the position of a set of points according to the target status, e.g., by marking attachment points according to the target status.

| LIST OF REFERENCE SIGNS | |
|---|---|
| 1 | optical head mounted display ("OHMD") |
| 14 | pupil sensor |
| 15 | hardware button |
| 16 | gaze button |
| 18 | camera |
| 2 | ARS |
| 3 | tracking system ("TS") |
| 31 | emitter |
| 32 | sensor |
| 4 | processing unit |
| 40 | CPU |
| 41 | volatile memory |
| 44 | non-volatile memory |
| 48 | bus |
| 5 | position marker |
| 51 | position and orientation marker ("POM") |
| 52 | stick |
| 53 | pointer |
| 551 | first part of the position marker |
| 5511 | head |
| 5512 | shaft |
| 552 | second part of the position marker |
| 7 | stabilizer device/blank |
| 73 | French bender |
| 8 | point |
| 80 | geometric shape/template |
| 9 | implant/attachment implant |
| 90 | attachment point |
| 91 | bone/vertebra |

The invention claimed is:

1. A method for supporting medical interventions using an augmented reality system, comprising:
determining, using a position marker and an electronic tracking system of the augmented reality system, positions of a set of points, wherein at least one point of the set of points is an attachment point of a pedicle screw;
calculating a template of a shape of a rod for stabilizing bones of a vertebrae using the determined positions of the set of points wherein the template of a shape of a rod comprises the determined positions of the set of points; and
displaying, on an optical head mounted display of the augmented reality system, the calculated template of a shape of a rod in the field of view of a bearer of the optical head mounted display, wherein the calculated template is displayed in a size that corresponds to a size of the rod at a distance between 1 cm and 100 cm from the optical head mounted display.

2. The method of claim 1, wherein the step of determining the positions of the set of points comprises:
positioning the position marker to a point;
measuring data concerning a position of the position marker using the tracking system; and
determining a position of the point using the measured data concerning the position of the position marker.

3. The method of claim 2, wherein the steps of positioning the position marker at a point and measuring data concerning a position of the position marker using the tracking system are iterated for each point of the set of points.

4. The method of claim 2, wherein the step of measuring data concerning a position of the position marker using the tracking system comprises measuring, using the tracking system, data concerning a position and orientation of a position and orientation marker that is fixedly attached to the position marker.

5. The method of claim 1, further comprising the formation of the rod according to the calculated template displayed on the optical head mounted display.

6. The method of claim 5, wherein the formation of the rod is based on a 3D-printing process according to the calculated template.

7. The method of claim 5, wherein the formation of the rod is based on a blank tool by using an adequate forming tool.

8. The method of claim 1, wherein the template is calculated using at least one of a Spline-curve, a Spline-surface, a composite Bézier-curve, and a composite Bézier-surface.

9. The method of claim 1, wherein calculating the template comprises using a pre-defined starting template.

10. The method of claim 9, wherein the pre-defined starting template is defined using medical imaging comprising at least one of X-ray/computed tomography ("CT") imaging and magnetic resonance imaging.

11. A system for supporting medical interventions, comprising:
a position marker; and
an augmented reality system, comprising:
an electronic tracking system that is adapted to measure data concerning a position of the position marker for a set of points, wherein at least one point of the set of points is an attachment point of a pedicle screw,
an optical head mounted display that is designed to display images in the field of view of its bearer, and
a processing unit that is configured:
to determine a position of the position marker using data measured by the tracking system,
to calculate a template of a shape of a rod for stabilizing bones of a vertebrae to be attached to the set of points wherein the template of a shape of a rod comprises the determined positions of the set of points, and
to create display information for the optical head mounted display of the calculated geometric shape in the field of view of the bearer,
wherein the calculated template is displayed in a size that corresponds to a size of the rod at a distance between 1 cm and 100 cm from the optical head mounted display.

12. The system of claim 11, wherein:
the position marker comprises a pointer and a position and orientation marker, wherein the pointer is fixedly attached to the position and orientation marker;
the tracking system is adapted to measure data concerning a position and orientation of the position and orientation marker;
the processing unit is configured to determine a position and orientation of the position and orientation marker using data measured by the tracking system; and
the processing unit is configured to determine a position of the pointer using a position and orientation of the position and orientation marker.

13. The system of claim 11, wherein the system comprises a memory element and wherein:
the memory element comprises data concerning the position of the pointer relative to the position and orientation of the position and orientation marker; and
the processing unit is configured to determine the position of the pointer using the position and orientation of the position and orientation marker and the data concerning the position of the pointer relative to the position and orientation of the position and orientation marker.

14. The system of claim 11, comprising one or more controllers, wherein the one or more controllers comprise at least one of a voice controller, a gesture controller, a gaze controller and/or a physical controller.

15. The system of claim 11, further comprising a 3D printer configured to form the rod based on a 3D-printing process according to the calculated template.

16. The system of claim 11, further comprising a blank and an adequate forming tool for forming the rod based on its representation in the optical head mounted display.

* * * * *